(12) United States Patent
Vogtmeier et al.

(10) Patent No.: US 11,189,391 B2
(45) Date of Patent: Nov. 30, 2021

(54) STRUCTURED GRATING COMPONENT, IMAGING SYSTEM AND MANUFACTURING METHOD

(71) Applicants: KONINKLIJKE PHILIPS N.V., Eindhoven (NL); NEDERLANDSE ORGANISATIE VOOR TOEGEPAST-NATUURWETEN-SCHAPPELIJK ONDERZOEK TNO, The Hague (NL)

(72) Inventors: Gereon Vogtmeier, Aachen (DE); Dorothee Hermes, Endhoven (NL); Bo Liu, Waalre (NL); Andre Yaroshenko, Garching (DE); Sandeep Unnikrishnan, Veldhoven (NL); Johannes Wilhelmus Maria Jacobs, Bostel (NL)

(73) Assignees: KONINKLIJKE PHILIPS N.V., Eindhoven (NL); NEDERLANDSE ORGANISATIE VOOR TOEGEPAST-NATUURWETEN-SCHAPPELIJK ONDERZOEK, The Hague (NL)

(*) Notice: Subject to any disclaimer, the term of this patent is extended or adjusted under 35 U.S.C. 154(b) by 0 days.

(21) Appl. No.: 15/734,238

(22) PCT Filed: Nov. 11, 2019

(86) PCT No.: PCT/EP2019/080772
§ 371 (c)(1),
(2) Date: Dec. 2, 2020

(87) PCT Pub. No.: WO2020/099280
PCT Pub. Date: May 22, 2020

(65) Prior Publication Data
US 2021/0313086 A1   Oct. 7, 2021

(30) Foreign Application Priority Data
Nov. 13, 2018   (EP) .................................... 18205877

(51) Int. Cl.
*G01K 1/06* (2006.01)
*G21K 1/06* (2006.01)
(Continued)

(52) U.S. Cl.
CPC ........... *G21K 1/067* (2013.01); *G02B 5/1838* (2013.01); *A61B 6/484* (2013.01); *G21K 2201/067* (2013.01); *G21K 2207/005* (2013.01)

(58) Field of Classification Search
None
See application file for complete search history.

(56) References Cited

U.S. PATENT DOCUMENTS 6,752,942 B2 * 6/2004 Kim .................... B81C 1/00031
264/112
7,820,064 B2   10/2010 Jin
(Continued)

FOREIGN PATENT DOCUMENTS

CN   102664054 A   9/2012
CN   106957051 A   7/2017
(Continued)

OTHER PUBLICATIONS

PCT International Search Report, International application No. PCT/EP2019/080772, dated Jan. 22, 2012.
(Continued)

*Primary Examiner* — Hoon K Song
(74) *Attorney, Agent, or Firm* — Larry Liberchuk

(57) ABSTRACT

The invention relates to a method of manufacturing a structured grating, a corresponding structured grating component (1) and an imaging system. The method comprising the steps of: providing (110, 120, 130) a catalyst (30) on a substrate (20), the catalyst (20) having a grating pattern; growing (140) nanostructures (50) on the catalyst (30) so as
(Continued)

to form walls (52) and trenches (54) based on the grating pattern; and filling (160) the trenches (54) between the walls (52) of nanostructures (50) using an X-ray absorbing material (70). The invention provides an improved method for manufacturing a structured grating and such structured grating component (1), which is particularly suitable for dark-field X-ray imaging or phase-contrast imaging.

14 Claims, 2 Drawing Sheets

(51) Int. Cl.
  *G02B 5/18* (2006.01)
  *A61B 6/00* (2006.01)

(56) References Cited

U.S. PATENT DOCUMENTS

| | | | |
|---|---|---|---|
| 8,069,782 B2 * | 12/2011 | Fragala | G06K 1/12 101/28 |
| 2004/0231781 A1 * | 11/2004 | Bao | G03F 7/0002 156/230 |
| 2006/0279843 A1 * | 12/2006 | Kurt | G02B 5/1847 359/558 |
| 2009/0086923 A1 | 4/2009 | Davis | |
| 2011/0189702 A1 | 8/2011 | Sun | |
| 2012/0307966 A1 | 12/2012 | Roessl | |
| 2013/0051530 A1 | 2/2013 | Nepomnishy | |
| 2018/0187294 A1 | 7/2018 | Kato | |

FOREIGN PATENT DOCUMENTS

| | | |
|---|---|---|
| WO | WO2017036729 A1 | 3/2017 |
| WO | WO2018111170 A1 | 6/2018 |

OTHER PUBLICATIONS

Yaohu, Lei et al., "Improvement of Filling Bismuth for X-Ray Absorption Gratings Through the Enhancement of Wettability", Journal of Micromechanics and Microengineering, vol. 26, issue 6, Nov. 26, 2015.

Wataru Yashiro et al: "A Metallic Glass Grating for X-Ray Grating Interferometers Fabricated by Imprinting", Applied Physics Express, vol. 7, No. 3, Feb. 25, 2014 (Feb. 25, 2014), p. 032501, XP055340059.

Rutishauser S et al: "Fabrication of Two-Dimensional Hard X-Ray Diffraction Gratings", Microelectronic Engineering, vol. 101, Jan. 31, 2013 (Jan. 31, 2013), pp. 12-16, XP028946800.

Yaohu Lei et al: "Fabrication of X-Ray Absorption Gratings Via Micro-Casting for Grating-Based Phase Contrast Imaging", Journal of Micromechanics & Microengineering, Institute of Physics Publishing, Bristol, GB, vol. 24, No. 1, Nov. 27, 2013 (Nov. 27, 2013), p. 15007, XP020255919.

* cited by examiner

STRUCTURED GRATING COMPONENT, IMAGING SYSTEM AND MANUFACTURING METHOD

FIELD OF THE INVENTION

The present invention relates to a method of manufacturing a structured grating and a corresponding structured grating component. The invention applies particularly to the field of dark-field or phase-contrast X-ray imaging in medical applications, while the application is of course not limited to these fields and can be applied, for instance, to nondestructive testing (NDT).

BACKGROUND OF THE INVENTION

Dark-field X-ray imaging or phase-contrast imaging is known to require special grating components with trench/wall structures of few μm width and 200-300 μm depth, i.e. which have a very high depth to width aspect ratio. X-ray absorbance varies between walls and trenches such that an interference pattern created by a first or phase grating component can be analyzed using a second or analyzer grating component.

US 2012/0307966 A1 discloses an apparatus for phase-contrast imaging including grating components for X-ray dark-field imaging or phase-contrast imaging. The grating arrangements include a beam splitter grating and an analyzer grating.

US 2018/0187294 A1 discloses a process for producing a molded material that can form metallic glass material in a state of lower viscosity, and can manufacture a small structure of several 10 pm or less in a comparatively short time while precisely controlling shape thereof, by the process comprising a heating step of heating supercooled state metallic glass material or a solid metallic glass material at a temperature increase rate of 0.5 K/s to a temperature at or higher than a temperature at which a crystallization process for a supercooled liquid of the metallic glass material begins, and a molding step of transfer molding the metallic glass material until the crystallization process for the supercooled liquid of the metallic glass material has been completed.

It has been an object of the present invention to provide a method for manufacturing a structured grating and such structured grating component, which are particularly suitable for dark-field X-ray imaging or phase-contrast imaging, and which allow a more accessible grating manufacturing.

SUMMARY OF THE INVENTION

According to a first aspect, a method of manufacturing a structured grating is provided, the method comprising the steps of:
 providing a catalyst on a substrate, the catalyst having a grating pattern,
 growing nanostructures on the catalyst so as to form walls and trenches based on the grating pattern, and
 filling the trenches between the walls of nanostructures using an X-ray absorbing material.

Since the nanostructures are grown corresponding to the grating pattern, they form walls with an X-ray absorbance corresponding to the X-ray absorbance of the nanostructures. Since furthermore the trenches between the walls are filled using an X-ray absorbing material, i.e. a material with at least higher X-ray absorbance than the nanostructure material, a grating component suitable for, for instance, dark-field X-ray imaging can be obtained. The method according to this aspect allows thus obtaining a structured grating with advantageous properties, while keeping complexity of the method to a minimum.

The substrate is particularly a conductive substrate, wherein the substrate can be a rigid substrate like conductive silicon with a plating base comprising, for instance, copper (Cu) nickel (Ni), gold (Au). The substrate can alternatively or additionally comprise a conductive foil, including a nickel foil and/or a copper foil, wherein the substrate then optionally comprises an insulator underneath the conductive foil.

The catalyst is preferentially provided in form of a sublayer on top of the substrate, wherein the catalyst is configured for the nanostructure growing process. Preferentially, nanostructures are grown on the catalyst. Expressed differently, no nanostructures will be grown on regions on the substrate, at which no catalyst is provided.

Preferentially, the nanostructures are grown normal to a surface of the substrate, while growing nanostructures under a particular angle is also contemplated. In particular, angled nanostructures can be grown by, for instance, providing a catalyst with an inclined shape with respect to the substrate or by different methods.

The grating pattern preferentially comprises longitudinal grating elements, which are at least one of elongated and parallel. The grating pattern is intended to cover all understandings of a grating for a person skilled in the art, while the entire catalyst and substrate and also only substructures of the catalyst and the substrate can be provided in the form of a grating pattern.

In a preferred embodiment, the nanostructures are grown using a material having a lower X-ray absorbance than the X-ray absorbing material, in particular showing an X-ray absorbance being at least two times lower than the X-ray absorbance of the X-ray absorbing material.

Preferentially, the difference in X-ray absorbance allows the generation of the interference pattern, as suitable for, for instance, phase gratings in dark-field or phase-contrast imaging, and the generation of intensity changes, for instance relating to so called analyzer gratings in these applications. The term X-ray absorbance has the meaning generally applicable in the art. In particular, when comparing X-ray absorbance, preferentially the X-ray absorbance of a particular energy or wavelength is compared. More preferably, the X-ray absorbance of all energies or wavelengths to be used for the application of the structured grating is compared. Accordingly, most preferably, the nanostructures have a significantly lower X-ray absorbance than the X-ray absorbing material over the entire energy range, for which the structured grating is intended.

In a preferred embodiment, the nanostructures comprise or consist of carbon nanotubes (CNT). CNT is particularly suitable as the nanostructures nanostructure according to the invention due to its properties, in particular with respect to X-ray absorption. Further, CNT can be grown up to a high aspect ratio with high stability. All kinds of CNT are contemplated according to this embodiment, including single-walled CNT, double-walled CNT and combinations thereof. It is preferred for the CNT to be vertical CNT.

In a preferred embodiment, the method further includes a step of applying a passivation layer prior to filling the trenches using the X-ray absorbing material. The passivation layer preferentially supports the step of filling the trenches with X-ray absorbing material and therefore preferentially covers the walls of the nanostructures substantially entirely. More specifically, for the step of filling with X-ray absorbing material via, for instance, electroplating, a passivation layer is necessary as isolation material to allow electroplating only from bottom to top of the trenches and not from the sidewalls, i.e. the walls. Otherwise a complete filling without voids might be not possible.

In a preferred embodiment, the CNT are together with the applied passivation layer referred to as the nanostructures.

In a preferred embodiment, applying the passivation layer includes a step of chemical vapor deposition, in particular of atomic layer deposition (ALD).

Chemical vapor deposition and, in particular, ALD are well-known methods of depositing thin layers of material on substrates. Advantageously, a substantially homogenous thickness is achieved covering all walls of the nanostructures, respectively. The application of the passivation layer can, due to the method employed, be precisely controlled to stop also at a defined depth within the trenches, such that the passivation layer does not cover the substrate, which is preferentially conductive and thus not insulated due to the passivation layer applied thereon. Conductivity can, in some embodiments, be essential for the step of filling the trenches with X-ray absorbing material, such as for methods including electroplating. Further, the infiltration can be precisely controlled to stop at a defined thickness of the passivation layer.

In a preferred embodiment, the passivation layer is applied to a defined distance from the substrate, in particular, to a distance to less than 2 µm. Thus, electric connectivity of the substrate can be maintained, while securely protecting the nanostructures from reduction or oxidation.

Preferentially, the passivation material employed in the passivation layer includes at least one of aluminum oxide (Al2O3), titanium dioxide (TiO2), and silica (SiO2).

In a preferred embodiment, the step of filling the trenches comprises a step of electroplating.

Using electroplating for filling the trenches carries the advantage to securely and completely, i.e. without voids, fill the trenches with X-ray absorbing material. Since the substrate is conductive, it can be employed as one electrode for the electroplating process. Preferentially, the X-ray absorbing material used for electroplating includes at least one X-ray absorbing metal, more preferably at least one of gold (Au), lead (Pb), and bismuth (Bi), while also other elements, alloys or combinations thereof can be employed likewise. In some embodiments, a filling height of the X-ray absorbing material in the trenches can be defined by adjusting a time of theory, it could very well be that the gratings are not completely filled, but are filled just to a certain level, which is lower than the CNT structures In a preferred embodiment, the step of filling the trenches comprises a step of mechanical filling, in particular using mechanical stress, high temperature and underpressure.

Since this filling method does not rely on electroplating, the passivation layer is not necessarily to be provided, thus allowing to reduce the number of steps and the complexity of the manufacturing method as a whole. A comparable method of mechanically filling the trenches is disclosed in, for instance, Lei, Yaohu, et al. "Improvement of filling bismuth for X-ray absorption gratings through the enhancement of wettability." *Journal of Micromechanics and Microengineering* 26.6 (2016): 065011.

Further, in this embodiment, a passivation step including ALD can however advantageously additionally be employed. Instead of the aim of isolation or passivation, in this embodiment particularly wettability would be of importance for the nanostructures, e.g. the CNT structures, while the passivation step can lead to an improved wettability.

In a preferred embodiment, the step of filling the trenches comprises the steps of:
filling the trenches with a metal powder embedded in a binder substance,
baking the binder substance to achieve solid filling of the trenches.

In order to obtain a high density and in particular filling rate of metal in the final product within the trenches, the metal powder is preferentially fine, e.g. smaller than 25 microns on average in diameter. Preferentially, the average size of powder particles is even smaller, such as smaller than 5 microns. Thus, a high packing efficiency factor within the trenches can be achieved.

In a preferred embodiment, the step of filling the trenches comprises a step of imprinting of the grating structures using the grown nanostructures.

The alternative method according to this embodiment of imprinting the grating structures can be advantageously applied depending on mechanical properties of the material system. A similar concept with, however, a different approach is described by, for instance, Yashiro, Wataru, et al. "A metallic glass grating for x-ray grating interferometers fabricated by imprinting." *Applied Physics Express* 7.3 (2014): 032501.

In a preferred embodiment, an aspect ratio is defined as a ratio of a height of the walls to a thickness of the walls, wherein the step of growing the nanostructures is performed until the aspect ratio is at least 5, in particular at least 10 and preferentially at least 15.

With a height of the walls, an extension of the walls in a direction substantially normal to the surface of the substrate is defined. Further, a thickness of the walls is defined as the extension in a direction substantially perpendicular to a longitudinal extension of the walls. Preferably, length and thickness of the wall span a plane substantially parallel to a surface of the substrate, while the height is substantially perpendicular to this plane. All walls of the nanostructures can be equal in height and/or thickness, or different walls can have different heights and/or thicknesses, respectively. In other embodiments, also different duty cycles across the grating can be advantageous. In the case of different heights and/or thicknesses, the aspect ratio according to this embodiment is understood as the lowest aspect ratio, i.e. having the highest thickness and lowest height.

In a preferred embodiment, a thickness of the walls and a thickness of the trenches is approximately equal. Thus, it can be ensured that a difference in thickness among walls and trenches is significant, which could lead to e.g. an increased noise of the interference pattern or reduced absorption of the X-rays.

In the context of this application, approximately refers to a range of plus and minus 30% of the approximated value. Accordingly, the thickness of the walls and the thickness of the trenches can be equal or one of the two values can be larger/smaller by up to 30% of the respective other thickness. Preferentially, the thicknesses of walls and trenches are approximately constant over the entire grating structure. Preferentially, a variance of thicknesses of walls and/or trenches is lower than 10%, further preferably lower than 5%, of an average thickness, respectively.

In a preferred embodiment, the substrate is provided with a surface of at least 100 cm$^2$, preferentially of at least 43 cm times 43 cm.

Since the process of nanostructure growing, in particular the process of CNT growth, allows the generation of trench wall structures on a large area, the method according to this embodiment can allow manufacturing of a grating covering a full detector field, i.e. 43 cm times 43 cm, in a single processing step. Accordingly, imaging quality will be improved since no artefacts or the like occur at joints between bordering gratings, in case a plurality of gratings would be needed. Further, manufacturing costs can be reduced, since only a single component in a single manufacturing step becomes necessary.

In a preferred embodiment, the substrate is provided with a tiled structure allowing the formation of subareas of the substrate.

Since the substrate is provided with a tile structure, depending on yield and homogeneity, the subarea formation can be beneficial for bending and/or focusing the structured grating component.

In a preferred embodiment, the method further comprises a step of bending the grating structure so as to adjust to a cone beam of an X-ray source, i.e. to the geometry of the setup.

In a preferred embodiment, the step of bending the grating structure is performed using a mechanical frame setup.

In use, in particular within systems for dark-field X-ray imaging/phase-contrast imaging, the structured grating is typically mounted in front of the detector, wherein a distance between X-ray source and detector exceeds 2 meters. Thus, a focusing of the grating surface in direction of the focal spot point of the X-ray source is required. Preferentially, according to some embodiments of the present invention, the fully processed structure, which is already filled with X-ray absorbing material within the trenches, is bent, in order to arrive at a focused geometry. This process flow can also be referred to as "focus last" process flow. It should of course be contemplated that also different process flows, i.e. in which the focusing occurs prior to filling the trenches or different orders of steps, are contemplated.

In a preferred embodiment, the step of providing a catalyst on a substrate comprises the steps of
  providing a substrate, the substrate having at least a conductive surface,
  depositing the catalyst on the substrate,
  creating the grating pattern on the catalyst using lithography and etching.

According to this embodiment, the geometric preparation of the catalyst on the substrate is described in more detail. Following a sublayer or catalyst deposition, using lithography and etching technologies well-known in the art, the geometric grating pattern is obtained using available techniques.

According to a further aspect, a structured grating component is provided. The structured grating component comprises
  a substrate,
  a catalyst on the substrate, the catalyst having a grating pattern,
  nanostructures on the substrate forming walls and trenches based on the grating pattern, and
  X-ray absorbing material filling the trenches between the walls of nanostructures,
  wherein the nanostructures include carbon nanotubes (CNT).

The structured grating component according to this aspect is particularly suitable for dark-field imaging or related processes, without being limited to this application. Due to the provided nanostructures forming walls and trenches therebetween, which are filled with X-ray absorbing materials, an effective structured grating with simple structure is provided. Since nanostructures, such as CNT, allow manufacturing on a large area substrate, the structured grating component according to this aspect can have a large surface, such as including a full field grating suitable for X-ray imaging systems. The main problem solved by the structure grating component according to this aspect, is the large area, but very fine structuring of the grating with a very high aspect ratio of the trench/geometry, which is solved by growing nanostructures, including CNT.

The structured grating component according to this aspect can be employed both as a phase grating and an analyzer grating. Preferentially, the structured grating component is employed as an analyzer grating, wherein it beneficially leads, among other benefits, to an analysis with reduced noise.

In a preferred embodiment, the structured grating component further comprises:
  a passivation layer arranged between the X-ray absorbing material and the nanostructures.

In a preferred embodiment, the passivation layer comprises at least one of Al2O3, TiO2, and SiO2.

In a preferred embodiment, the substrate is in direct contact with the X-ray absorbing material.

The substrate, which is preferentially conductive in order to allow an electroplating process for filling the trenches with X-ray absorbing material, is thus maintained conductive, although a passivation layer protecting the nanostructures is applied. Preferentially, the passivation layer enters into the trenches and covers all walls and surfaces of the nanostructures, while a defined distance, such as below 2 microns, is maintained, at which the passivation coating stops, before covering the ground substrate. A precise control of the passivation layer can be achieved by, for instance, applying ALD technology.

In a preferred embodiment, the nanostructures comprise support elements joining two adjacent trench walls. The support structures improve the mechanical stability of the structured grating component.

In a preferred embodiment, the support elements are provided at different positions in a longitudinal direction on two opposite sides of a wall, respectively. Thus, the mechanical stability of the structured grating component can be further increased. At the same time, interference patterns in a direction perpendicular to the extension of the walls of the grating pattern can be reduced in case the structured grating are phase gratings. Likewise, in case the structured grating is an analyzer grating, background noise induced by the support elements can be reduced. Finally, it is preferred for two support elements joining the same walls, respectively, to have a significantly larger distance, e.g. a factor of more than 4, preferably more than 10, along the direction of the walls than a distance between two adjacent walls.

In a preferred embodiment, the substrate comprises at least one of a rigid substrate including conductive silicon and a conductive foil including nickel foil, copper foil.

In a preferred embodiment, in case the substrate comprises a rigid substrate, the substrate comprises a plating base, wherein the plating base in particular comprises at least one of the elements Cu, Ni, Au.

In a preferred embodiment, the substrate comprises at least one of the elements Cu, Ni, and Au.

In a preferred embodiment, the X-ray absorbing material comprises at least one of the elements Au, Pb, and Bi.

In a further aspect, an imaging system, in particular X-ray phase-contrast or dark-field imaging system, is provided. The imaging system comprises a structured grating component according to an aspect of the invention.

It shall be understood that the method of claim 1, the structured grating component of claim 10 and the imaging system of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

FIGS. 1A to 1F schematically and exemplarily illustrate the various steps of the method of manufacturing a structured grating according to the present invention.

Figure 1A:
FIG. 1A-1F schematically and exemplarily illustrate steps of a method according to the invention, FIG. 2 schematically and exemplarily illustrates a top view on an unfilled structured grating component, and FIG. 3 schematically and exemplarily illustrates a perspective view of a cross-sectional cut through a structured grating.

As illustrated in FIG. 1A, in a step 110, a substrate 20 is provided with a catalyst 30 on a surface thereof. Substrate 20 can be a rigid substrate like conductive silicon with a plating base, comprising for instance Cu, Ni, Au, wherein the catalyst 30 forms a sublayer for the growing process of nanostructures 50 described below, such as carbon nanotubes (CNT). Substrate 20 can also be or comprise a conductive foil including nickel foil, copper foil, and the like.

Figure 1B:
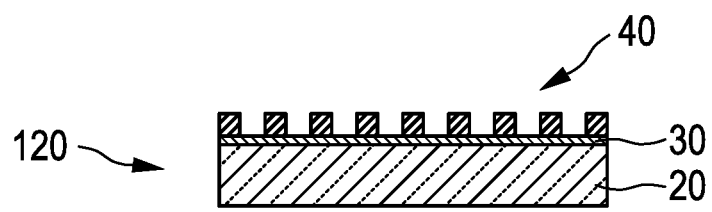

In FIG. 1B, a lithography step 120 of applying a photo mask 40 having a grating structure, i.e. comprising the geometric structure with which the catalyst 30 is to be patterned, is applied.

Figure 1C:
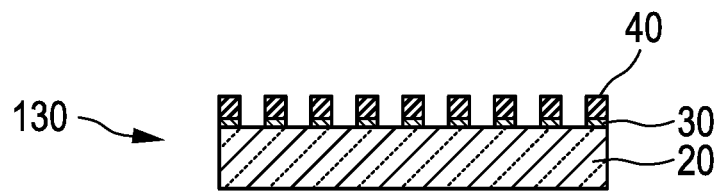

In an etching step 130, which is schematically and exemplarily illustrated in FIG. 1C, light is subjected onto the arrangement such that all parts of the catalyst 30, which are not covered by photo mask 40, are removed or etched. Steps 110 to 130 can be summarized as geometric preparation of a catalyst 30 having a grating pattern on a substrate 20.

Figure 1D:
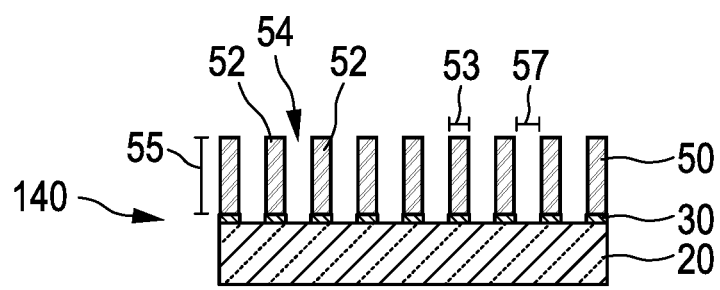

In FIG. 1D, a step 140 of growing nanostructures 50 on catalyst 30 is schematically and exemplarily illustrated. Walls 52 and trenches 54 located between two adjacent walls 52 are thus formed. Walls 52 grow on top of catalyst 30 based on the grating pattern provided for this purpose.

Preferentially, nanostructures 50 comprise or consist of carbon nanotubes (CNT). Thus, the growing step 140 is specifically adapted for the growth of CNT. CNT allow the deposition and growth of walls 52 with a very high aspect ratio, i.e. a very high ratio of a thickness 53 to a height 55 of the walls 52, respectively. The grating pattern is formed such that thickness 53 approximately corresponds to a distance 57 between two adjacent walls 52.

Figure 1E:
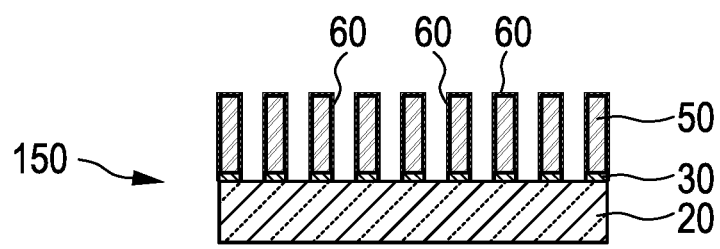

FIG. 1E schematically and exemplarily illustrates an optional step 150 of preparing the structures for filling with X-ray absorbing materials. More specifically, a passivation layer 60 is applied including the infiltration of nanostructures 50 at the side surfaces of the walls 52 and the topside of the walls 52. Passivation layer 60 is applied, for instance, using atomic layer deposition (ALD) or comparable technologies. The infiltration is precisely controlled to stop also at a defined depth as well as the passivation layer 60 on the sidewalls of the walls 52 is precisely controlled to stop in a defined distance from substrate 20, preferably below 2 microns, before covering the ground of the trench 54 and thus contact substrate 20. Thus, electronic and conductivity properties of substrate 20 are not obstructed by passivation layer 60.

Figure 1F:
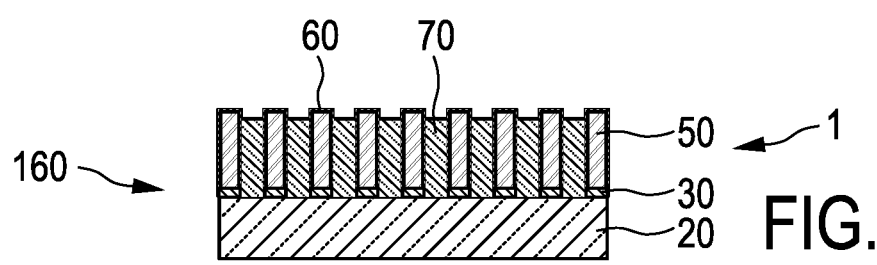

FIG. 1F schematically and exemplarily illustrates a step 160 of filling the trenches 54 between walls 52 of nanostructures 50 using an X-ray absorbing material 70. A plurality of alternatives for filling the trenches 54 in step 160 is described in the following.

The passivation material of passivation layer 60 preferentially comprises at least one of Al2O3, TiO2, and SiO2.

Step 160 preferentially comprises a step of electroplating. Electroplating allows for a complete and reliable filling of the trenches 54 with X-ray absorbing material 70.

An alternative to electroplating for step 160 includes mechanical filling using mechanical stress, high temperature and underpressure, as described in the above cited article by Lei et al., 2016. An even further approach includes filling the trenches in step 160 using a fine powder of metal, for instance in a binder matrix that can be baked at the end, in order to achieve a solid filling with X-ray absorbing material 70 of the trenches 54. A further alternative method of step 160 includes the use of the nanostructures 50 for imprinting of the grating structures. This alternative depends on mechanical properties of the material system. A similar concept, but approached different from this method is described by the above cited article by Yashiro et al. 2014.

The X-ray absorbing material 70 comprises for example Au, Pb, Bi, or any combination or alloy thereof. In particular, the composition of X-ray absorbing material 70 can be chosen in order to have the most favorable X-ray absorbance for the intended application.

Step 150 is strictly required in case the electroplating is employed as an implementation of step 160 for filling the trenches 54. In the alternative versions of step 160, passivation of step 150 may not be required for all implementations. For these methods, in several examples, it is more important to guarantee wettability of the nanostructures 50 with the filling material forming X-ray absorbing material 70 to avoid defects in filling due to differences in respective material properties. Therefore, step 150 can, for other methods of filling in step 160 apart from electroplating, additionally or alternatively employ the deposition of an optional nanolayer over all on the nanostructures 50, so as to improve the wettability of the respective nanostructures 50.

After filling the trenches 54 in step 160, manufacturing of a structured grating component 1 is completed.

Figure 2:
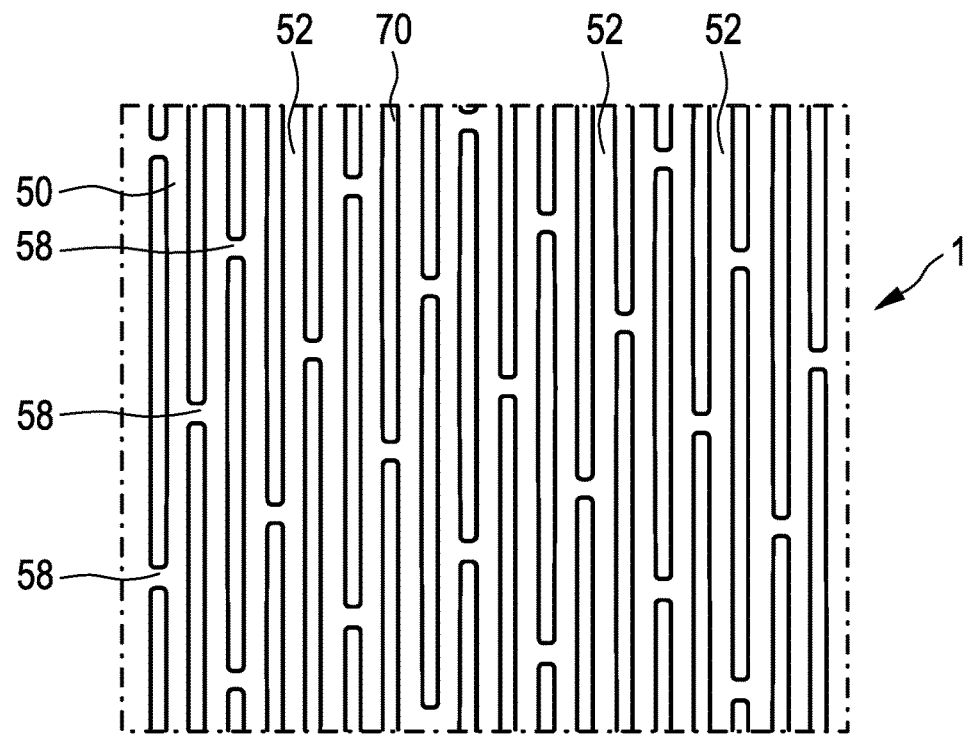

FIG. 2 schematically and exemplarily illustrates a topview on structured grating component 1 corresponding to the result of the method explained in FIGS. 1A to 1F. A plurality of longitudinal and parallel walls 52 can be seen as extending in the direction illustrated as vertical in FIG. 2, wherein X-ray absorbing material 70 is illustrated in the trenches between respective walls 52. At respective different positions along the extension direction of walls 52, support elements 58 are provided, which join or link adjacent walls 52. Thus, a mechanical stability of structured grating component 1 is increased.

Preferentially, the thickness of walls and trenches, respectively, is in the range of 1 to 10 microns, preferably between 7 and 9 microns, wherein a deviation from the standard or average thickness is preferentially less than 10%. Thus, the thickness of walls and trenches can be considered to be approximately constant.

Figure 3:
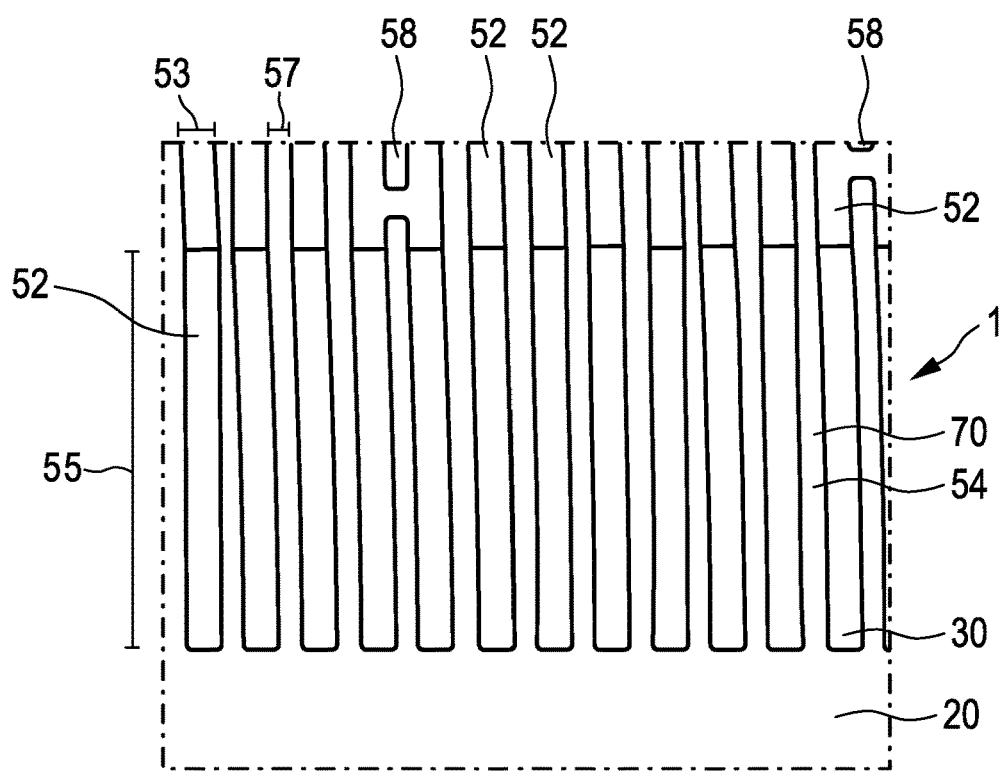

FIG. 3 schematically and exemplarily illustrates structured grating component 1 in a perspective, cross-sectional view such that the extension of walls 52 and trenches 54 in a normal direction on substrate 20 can be seen. The heights 55 of walls 52 are larger than their respective widths or thickness, wherein the aspect ratio is larger than 5, preferably larger than 10 and most preferably at least 15.

For the integration of such structured grating component 1 in an X-ray imaging system, substrate 20 can preferably be bent to a defined radius to match a focus to the focal spot distance. Preferentially, substrate 20 can be bent after manufacturing structured grating component 1 according to the method as described with reference to FIG. 1, wherein stable structures of a bottom layer at the interface between substrate 20 and nanostructures 40 will support the bending.

Infiltration and step 160, including electroplating or any other method of filling the trenches 54 with nanostructures 70, could stabilize the mechanical interface depending on an optimization recipe. Preferentially, substrate 20 can be bent using a mechanical frame setup. In some examples, substrate 20 can also be patterned in tiles to form subareas, which can be individually used for bending.

While the main focus of the concepts according to the invention as described above is medical X-ray imaging, in particular phase-contrast imaging and dark-field imaging, other use cases for the inventive concepts are manifold. Apart from medical imaging, application of the inventive concepts is also beneficial, for instance, in nondestructive testing (NDT).

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method of manufacturing a structured grating, the method comprising:
    providing a catalyst on a substrate, the catalyst having a grating pattern;
    growing nanostructures on the catalyst so as to form walls and trenches based on the grating pattern; and
    filling the trenches between the walls of nanostructures using an X-ray absorbing material.

2. The method according to claim 1, wherein the nanostructures are grown using a material having a lower X-ray absorbance than the X-ray absorbing material.

3. The method according to claim 1, wherein the nanostructures comprise carbon nanotubes.

4. The method according to claim 1, further including applying a passivation layer prior to filling the trenches using the X-ray absorbing material.

5. The method according to claim 4, wherein applying the passivation layer includes a chemical vapor deposition.

6. The method according to claim 4, wherein the passivation layer is applied to a defined distance from the substrate, wherein the defined distance particular less than 2 µm.

7. The method according to claim 4, wherein filling the trenches comprises electroplating.

8. The method according to claim 1, wherein filling the trenches comprises at least one of:
    mechanical filling using mechanical stress, high temperature and underpressure;
    filling the trenches with a metal powder embedded in a binder substance and baking the binder substance to achieve solid filling of the trenches; and
    imprinting the grating structures using the grown nanostructures.

9. The method according to claim 1, further comprising bending the grating structure to adjust the grating structure to a cone beam of an X-ray source.

10. A structured grating component, comprising:
    a substrate;
    a catalyst on the substrate, the catalyst having a grating pattern;
    nanostructures on the substrate forming walls and trenches based on the grating pattern; and
    X-ray absorbing material filling the trenches between the walls of nanostructures,
    wherein the nanostructures include carbon nanotubes.

11. The structured grating component according to claim 10, further comprising:
    a passivation layer arranged between the X-ray absorbing material and the nanostructures.

12. The structured grating component according to claim 10, wherein the substrate is in direct contact with the X-ray absorbing material.

13. The structured grating component according to claim 10, wherein the nanostructures comprise support elements joining two adjacent walls, wherein the support elements are provided at different positions in a longitudinal direction on two opposite sides of a wall, respectively.

14. An imaging system, comprising a structured grating component according to claim 10.

* * * * *